United States Patent [19]

Bogeso

[11] Patent Number: 4,650,884
[45] Date of Patent: Mar. 17, 1987

[54] NOVEL INTERMEDIATE AND METHOD FOR ITS PREPARATION

[75] Inventor: Klaus P. Bogeso, Lyngby, Denmark

[73] Assignee: H. Lundbeck A/S, Copenhagen-Valby, Denmark

[21] Appl. No.: 761,774

[22] Filed: Aug. 2, 1985

[30] Foreign Application Priority Data

Aug. 6, 1984 [GB] United Kingdom ............... 8419963

[51] Int. Cl.⁴ .................. C07D 307/87; C07C 121/80
[52] U.S. Cl. .................................... 549/467; 558/422
[58] Field of Search ................. 260/465 E; 549/467; 558/422

[56] References Cited

U.S. PATENT DOCUMENTS 4,136,193  1/1979  Bogeso et al. ...................... 549/467

Primary Examiner—Dolph H. Torrence
Attorney, Agent, or Firm—Gordon W. Hueschen

[57] ABSTRACT

The present invention relates to the novel compound of the following formula:

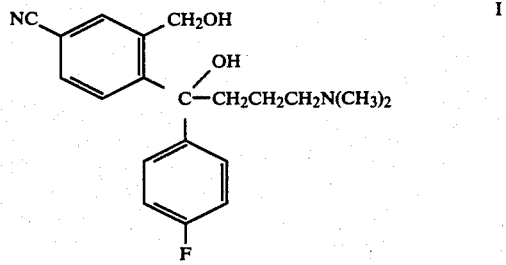

as well as acid addition salts thereof, a method for the preparation of the compound of Formula I, and to the use of said novel compound in the preparation of the known antidepressant drug 1-(3-dimethylaminopropyl)-1-(4'-fluorophenyl)-1,3-dihydroisobenzofuran-5-carbonitrile, or a pharmaceutically acceptable acid addition salt thereof.

3 Claims, No Drawings

NOVEL INTERMEDIATE AND METHOD FOR ITS PREPARATION

BACKGROUND OF THE INVENTION

The preparation and properties of antidepressant substituted 1-dimethylaminopropyl-1-phenylphthalans (or 1-(3-dimethylaminopropyl)-1-phenyl-1,3-dihydroisobenzofurans) have been described in U.S. Pat. No. 4,136,193. The most interesting of these compounds contain a cyano-group, and one of these, 1-(3-dimethylaminopropyl)-1-(4'-fluorophenyl)-1,3-dihydroisobenzofuran-5-carbonitrile, has shown great promise as a valuable antidepressant drug with few side effects.

It has been found, however, that the methods described in U.S. Pat. No. 4,136,193 for the preparation of this compound possess some problems in the scale-up to commercial production, and this has necessitated further research in an attempt to discover a shorter route to this compound and to avoid the risk involved in the metalation step used previously.

SUMMARY OF THE INVENTION

It is an established fact that the cyano-group of aromatic nitriles is very sensitive to attack by a number of organic as well as inorganic compounds (see for example "Methoden der Organischen Chemie", Houben-Weyl, Vol. 8, 345–51, 429, Georg-Thieme Verlag, Stuttgart (1952)).

For example, nitriles may be attacked by Grignard reagents to give ketimines which can be hydrolyzed to ketones. This method is a recommended standard method for preparation of ketones ("Methoden der Organischen Chemie", Houben-Weyl, Vol. 13/2a, 353–366, Georg-Thieme Verlag, Stuttgart (1973)). Actually, advantage of this invention has already been taken (as mentioned in U.S. Pat. No. 4,136,193) with molecules closely related to those of the present invention.

It is also wellknown that treatment of nitriles with strong acids such as high-percentage sulfuric acid normally will hydrolyze the nitrile-group to a carboxylic acid amide or a carboxylic acid.

The most useful method of preparation described in U.S. Pat. No. 4,136,193 involves Grignard reactions as well as treatment with strong acid, but the nitrile group was always introduced subsequent to such steps because of the known reactivity of the nitrile group described above. Typically, the cyano-group was introduced by reaction of a halogen substituted phthalane (as for example 1-(4'-fluorophenyl)-5-bromophthalane) with cuprous cyanide in DMF to yield a cyano-phthalane (as for example 1-(4'-fluorophenyl)-5-phthalanecarbonitrile) which was metalated and then alkylated through reaction with 3-dimethylaminopropyl chloride to yield the desired 1-(3-dimethylaminopropyl)-1-phenylphthalan, especially 1-(3-dimethylaminopropyl)-1-(4'-fluorophenyl)-5-phthalancarbonitrile.

According to the method of the present invention it has now surprisingly been found that cyano-substituted compounds can be prepared in good yields by the following route:

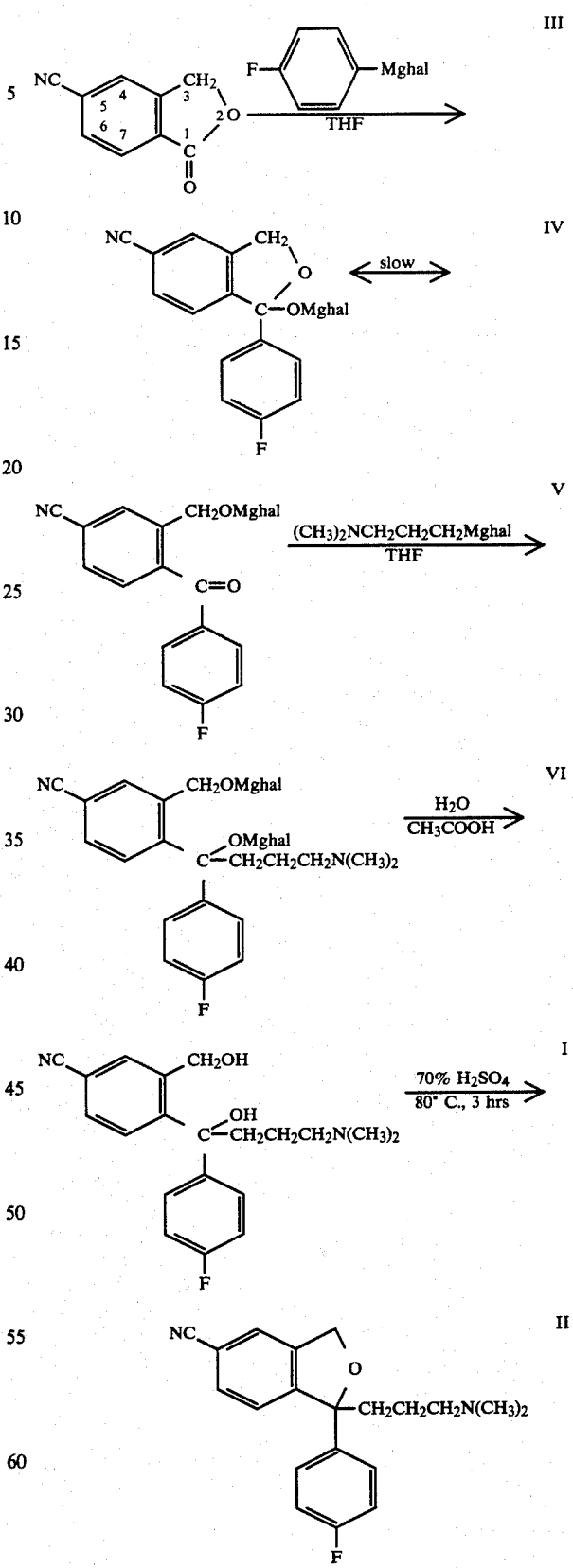

The compound of Formula II is the wellknown antidepressant drug 1-(3-dimethylaminopropyl)-1-(4'-fluorophenyl)-1,3-dihydroisobenzofuran-5-carbonitrile.

The 5-cyanophthalide (Formula III) used as a starting material is a known compound (Tirouflet, J.; Bull.Soc.-Sci.Bretagne 26, 35, (1951).

In the formulas IV, V and VI "hal" means halogen, preferably chlorine or bromine. It is, indeed, surprising that only modest amounts of biproducts are formed by reaction of the cyano-group with the two Grignard-reagents involved. Of similar great importance to the success of this scheme is the surprisingly low rate of ring opening of the addition product formed in the first Grignard step (Formula IV). Actually, it is very convenient from a practical point of view to be able to run these two Grignard reactions in succession in the same vessel.

The novel intermediate (of Formula I) produced in the combined Grignard steps may be isolated and purified as described below. However, it is far more convenient to proceed with the ring closure of the crude material.

The cyano-group also shows a surprising resistance to the rather drastic and prolonged treatment with strong acid in the step of ring closure.

With careful control of the reaction conditions involved this process has already been shown to be very reliable on a technical scale as evidenced by smooth performance, stable yields and high purity of the final product (Formula II) produced.

The following examples are given by way of illustration only and are not to be construed as limiting;

EXAMPLE 1

4-[4-(Dimethylamino)-1-(4'-fluorophenyl)-1-hydroxybutyl]-3-(hydroxymethyl)-benzonitrile A Grignard solution is prepared by addition of 1-bromo-4-fluorobenzene (594 g, 3.4 mole) in dry tetrahydrofuran (1.6 liters) to a suspension of magnesium turnings (101 g, 4.15 mole) in dry tetrahydrofuran (250 ml) at reflux. When all has been added the solution is left stirring for 30 minutes without cooling or heating, and is then filtered to remove excess magnesium turnings. The Grignard solution is added to a nitrogen purged slurry of 5-cyanophthalide (450 g, 2.83 mole) in dry tetrahydrofuran (2.9 liters) in the course of 3 hours. The temperature is kept at 0°–3° C. during the addition after which the reaction mixture is stirred for 30 min. without cooling and then left standing overnight.

The same day a second Grignard solution is prepared from 3-dimethylaminopropyl chloride (342 g, 2.81 mol) and magnesium turnings (81 g, 3.3 mol) in dry tetrahydrofuran (1.15 liters). Next day the filtered solution of 3-dimethylaminopropylmagnesium chloride is added in the course of 6 hours to the reaction mixture obtained in the first Grignard reaction. The temperature is kept at 10°–12° C. during the addition whereupon the mixture is stirred for 30 minutes without cooling, and is then left overnight at room temperature without stirring. The reaction mixture is poured into icewater (2 kg ice, 3 liters water) whereupon acetic acid (700 ml, 80% by weight) is added, resulting in a final pH of 6.5–7.0 in the solution. Tetrahydrofuran is then distilled until a maximum pot temperature of 50° C. at 60 mm Hg is reached, whereupon toluene (4.5 liters) is added to the mixture. Aqueous ammonia (300 ml, 25% by weight) is then added to give a final pH of 9 in the water layer, the temperature is adjusted to 45°–50° C., and the mixture is stirred for 15 minutes. The toluene layer is separated, and the aqueous layer is extracted once with toluene (600 ml). The combined toluene extracts are washed with warm (50° C.) water (600 ml) and are then extracted with dilute acetic acid (2.5 liters water and 800 ml acetic acid, 80% by weight). The acetic extract is separated and combined with toluene (3.8 liters), whereupon aqueous ammonia (900 ml, 25% by weight) is added to give a final pH of 9 or higher in the water layer. The toluene phase is separated, and the water layer is extracted once with toluene (600 ml), whereupon the combined toluene extracts are washed four times with warm (50° C.) water (4×1 liter). This toluene solution is normally used directly in the next step.

If desired, the title compound can be isolated and purified in the following manner:

The warm toluene solution from above is stirred for 30 min. at 60° C. with charcoal (50 g) and silica gel (150 g, Merck Darmstadt No. 7734) and then filtered by suction on a filter pretreated with filter aid. This treatment is repeated with charcoal (25 g) and silica gel (90 g). After filtration the toluene is removed at reduced pressure (20 mm Hg) to a maximum of 60° C. The resulting oil (640 g) is dissolved in boiling diethyl ether (1500 ml) and this solution is stirred vigorously with water (1500 ml) while adding 47% aqueous hydrogen bromide (190 ml) during 10 min. at 27°–34° C. Diethyl ether is then distilled at reduced pressure at 33°–35° C. Additional water (500 ml) is added, and the mixture is cooled to 11° C. After 18 hours the crystals are collected on a suction filter. The wet cake is recrystallized from water (1500 ml) with the use of charcoal (37 g) and then dried for 23 hours in a vacuum oven at 50° C. and 220 mm Hg. Yield: 525 g of solid material which is purified further from a hot mixture of 2-propanol (9.5 liters) and ethanol (2.73 liters) with the use of charcoal (82 g) and silica gel (191 g) after which the filtrate is mixed with hexane (2 liters) and then cooled to 12° C. The crystals are isolated by suction and then dried in vacuum (200 mm Hg) at room temperature.

Yield of 4-[4-(dimethylamino)-1-(4'-fluorophenyl)-1-hydroxybutyl]-3-(hydroxymethyl)benzonitrile, hydrobromide: 425 g. MP 205°–206° C.

Elemental analysis ($C_{20}H_{23}FN_2O_2HBr$):

|  | Found | Calculated |
| --- | --- | --- |
| % C | 56.21 | 56.74 |
| % H | 5.69 | 5.73 |
| % N | 6.33 | 6.61 |
| % Br | 18.86 | 18.87 |

$^1$H-NMR (DMSO-d$_6$, Me$_4$Si as internal reference standard): 1.1–1.9 ppm (m, 2H, —CH$_2$—CH$_2$—CH$_2$N<), 2.1–2.45 ppm (broad t, 2H,>$\overline{COH}$—CH$_2$—CH$_2$—), 2.6–2.8 ppm (s, 6H, —N(CH$_3$)$_2$), 2.85–3.2 ppm (broad t, 2H, —CH$_2$N<), 3.85–4.75 ppm (broad q, 2H, —CH$_2$OH), 5.0–5.4 ppm (broad s, 1H, —OH), 5.8–6.2 ppm (broad s, 1H, —OH), 6.95–7.5 ppm (m, 4H, aromatic), 7.7–8.0 ppm (m, 3H, aromatic), 9.0–9.75 (broad s, 1H, $$\diagdown \overset{+}{\underset{\diagup}{N}H}).$$

HPLC-analysis (Spherisorb S 5 W; Mobile phase: Heptane-propanol-2-aqueous ammonia-H$_2$O, 85:15:0.4:0.2, UV$_{254}$ detector) showed a content of 99.6% of the title compound.

EXAMPLE 2

1-(3-Dimethylaminopropyl)-1-(4'-fluorophenyl)-1,3-dihydroisobenzofuran-5-carbonitrile hydrobromide The toluene solution containing the crude product mentioned in Example 1 is heated to 50° C., and 70% sulfuric acid (made from 321 g of 96% sulfuric acid and 119 g ice) is added while stirring. The mixture is heated to 80° C. and kept at this temperature for 3 hours, whereupon it is cooled to about 30° C. Cold water (600 ml) and aqueous ammonia (600 ml, 25% by weight) are then added, and the mixture (pH 10) is stirred at 50°-60° C. for 15 minutes. The water phase is discarded, and the toluene layer is washed 5 times with warm water (5×1 liter). The organic phase is dried over anhydrous sodium sulfate, filtered and stirred for 1 hour with silica gel (375 g). The mixture is filtered by gravity on a filter precharged with silica gel (188 g). The filter is rinsed with toluene (3.4 liters) and the combined filtrates are evaporated under reduced pressure (30 mm Hg) until a maximum temperature of 50° C. is reached. The residue is then dissolved in acetone (2 liters) and filtered with charcoal. The filtrate is cooled to 20° C. Gaseous hydrogen bromide (130-140 g) is then introduced during 2 hours at 20°-25° C. until pH is 3, and pH is then adjusted to 7 by adding some of the acetone solution of the title compound. The mixture is left crystallizing overnight whereupon the crystals are filtered and washed with hexane (750 ml) and then with acetone (750 ml). After drying at 45° C. a yield of 610-650 g crude title compound is obtained. This material is dissolved in water (1.8 liters) at about 55° C. and is then filtered with charcoal, cooled to 20° C. and left overnight for crystallization after addition of seed crystals. The crystals are filtered, washed with water (350 ml) and dried. Yield: 560-570 g.

The crystals from the 1st recrystallization are dissolved in a mixture of methanol (1.7 liters) and 2-propanol (3.4 liters) at 70° C., and are then filtered with charcoal, cooled to 20° C. and left for crystallization overnight. The crystals are filtered and washed with a mixture of methanol (150 ml) and 2-propanol (300 ml). After drying there is obtained 510-520 g of purified material.

The material from the 2nd recrystallization is dissolved in a mixture of methanol (510 ml) and acetone (2.04 liters) at 55° C. and is then filtered with charcoal. The filtrate is cooled to 20° C., and after addition of seed crystals hexane (4.1 liters) is slowly added during 1 hour. After crystallization overnight the crystals are filtered and washed first with a mixture of acetone (150 ml) and hexane (300 ml), and then washed two times with hexane (2×300 ml). After drying there is obtained 470-480 g of pure (1-(3-dimethylaminopropyl)-1-(4'-fluorophenyl)-1,3-dihydroisobenzofuran-5-carbonitrile, hydrobromide, MP 185°-186° C.

I claim:

1. A compound of the following formula:

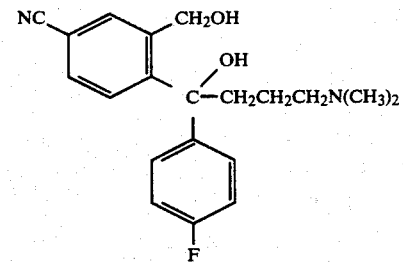

or an acid addition salt thereof.

2. A method for the preparation of a compound of claim 1, characterized thereby that 5-cyanophthalide is reacted with a Grignard solution containing a 4-fluorophenyl magnesium halide, whereupon the resulting mixture containing the compounds of the following structures in equilibrium

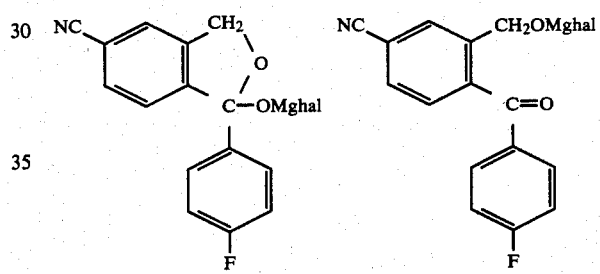

is reacted with a Grignard solution containing a 3-dimethylaminopropyl magnesium halide, the reaction mixture hydrolyzed and the resulting 4-[4-(dimethylamino)-1-(4'-fluorophenyl)-1-hydroxybutyl]-3-(hydroxymethyl)-benzonitrile isolated as the free base, or an acid addition salt thereof.

3. In a method for the preparation of the compound 1-(3-dimethylaminopropyl)-1-(4'-fluorophenyl)-1,3-dihydroisobenzofuran-5-carbonitrile, or a pharmaceutically-acceptable acid addition salt thereof, the step of effecting ring-closure by dehydration of a compound of claim 1 by reacting the same with strong sulfuric acid.

* * * * *